(12) United States Patent
Jensen et al.

(10) Patent No.: US 9,295,620 B2
(45) Date of Patent: Mar. 29, 2016

(54) DENTAL TREATMENT COMPOSITIONS AND CONFORMABLE DENTAL TREATMENT TRAYS USING THE SAME

(75) Inventors: Steven D. Jensen, South Jordan, UT (US); Densen Cao, Sandy, UT (US)

(73) Assignee: CAO Group, Inc., West Jordan, UT (US)

( * ) Notice: Subject to any disclaimer, the term of this patent is extended or adjusted under 35 U.S.C. 154(b) by 965 days.

(21) Appl. No.: 12/329,583

(22) Filed: Dec. 6, 2008

(65) Prior Publication Data

US 2009/0087393 A1 Apr. 2, 2009

Related U.S. Application Data

(63) Continuation of application No. 12/329,582, filed on Dec. 6, 2008, which is a continuation-in-part of application No. 11/307,463, filed on Feb. 8, 2006, now abandoned.

(51) Int. Cl.
| | |
|---|---|
| *A61K 8/21* | (2006.01) |
| *A61Q 11/00* | (2006.01) |
| *A61K 8/22* | (2006.01) |
| *A61K 8/84* | (2006.01) |
| *A61Q 5/08* | (2006.01) |
| *A61Q 11/02* | (2006.01) |
| *A61K 8/49* | (2006.01) |

(52) U.S. Cl.
CPC ... *A61K 8/22* (2013.01); *A61K 8/49* (2013.01); *A61K 8/84* (2013.01); *A61Q 5/08* (2013.01); *A61Q 11/00* (2013.01); *A61Q 11/02* (2013.01); *A61K 2800/48* (2013.01)

(58) Field of Classification Search
USPC .............. 424/49, 52; 433/215, 217.1
See application file for complete search history.

(56) References Cited

U.S. PATENT DOCUMENTS

| | | | |
|---|---|---|---|
| 5,891,453 A | 4/1999 | Sagel et al. | |
| 5,894,017 A | 4/1999 | Sagel et al. | |
| 6,045,811 A | 4/2000 | Dirksing et al. | |
| 6,113,629 A * | 9/2000 | Ken | 623/1.1 |
| 6,136,297 A | 10/2000 | Sagel et al. | |
| 6,322,360 B1 | 11/2001 | Burgio | |
| 6,500,408 B2 | 12/2002 | Chen | |
| 6,514,483 B2 | 2/2003 | Xu et al. | |
| 6,582,708 B1 | 6/2003 | Sagel et al. | |
| 6,685,923 B2 | 2/2004 | Peterson et al. | |
| 6,730,316 B2 * | 5/2004 | Chen | 424/435 |
| 6,765,038 B2 | 7/2004 | Mitra | |
| 6,780,401 B2 | 8/2004 | Kim et al. | |
| 6,860,736 B2 * | 3/2005 | Allred et al. | 433/80 |
| 6,884,426 B2 | 4/2005 | Sagel et al. | |
| 7,056,118 B2 | 6/2006 | Allred et al. | |
| 7,059,857 B2 | 6/2006 | Allred et al. | |
| 7,122,199 B2 | 10/2006 | Sagel et al. | |
| 2002/0006387 A1 | 1/2002 | Sagel et al. | |
| 2007/0003495 A1 | 1/2007 | Sagel et al. | |
| 2007/0253990 A1 | 11/2007 | Sagel et al. | |
| 2007/0269471 A1 | 11/2007 | Sagel et al. | |

OTHER PUBLICATIONS

Aldrich Catalog 2005-2006, pp. 1-6 (catalog p. 1939), Dec. 2004, Received Mar. 2005.*

\* cited by examiner

*Primary Examiner* — Lezah Roberts

(74) *Attorney, Agent, or Firm* — CAO Group, Inc.

(57) ABSTRACT

The present invention is a formable dental treatment tray utilizing poly(2-ethyl-2-oxazoline) and a gelatinous active. Blending of the active is accomplished by mixing the Poly(2-ethyl-2-oxazoline) with an active ingredient, such as a peroxide like hydrogen peroxide, carbamide peroxide, sodium perborate, or sodium percarbonate, usually also with water or an appropriate organic solvent. Peroxide concentrations in these new gels can reach a 30% concentration of hydrogen peroxide while maintaining a shelf life of six months at room temperature without developing peroxide decomposition. The gels are applied to an appropriate backing and dried to a gelatinous state. In use, the active is hydrated and regains adhesiveness. Then the tray is pressed and formed around a user's dental arch to form the customizable tray. Multiple active ingredients may be used, with or without peroxide, for accomplishing desired treatment regimens.

6 Claims, 6 Drawing Sheets

DENTAL TREATMENT COMPOSITIONS AND CONFORMABLE DENTAL TREATMENT TRAYS USING THE SAME

CROSS-REFERENCES TO RELATED APPLICATIONS

This Application claims priority as a Continuing-in-part application of prior filed U.S. Non-provisional application Ser. No. 11/307,463, filed on Feb. 8, 2006. This parent application is expressly incorporated by reference herein in its entirety

FIELD OF THE INVENTION

The present invention relates to the field of thickeners and more particularly relates to a thickener for the production of a stable visco-elastic medium for the storage and delivery of peroxide and other active ingredients, particularly hydrogen peroxide and its adducts in the form of a dental tray, and the products manufactured using the same.

BACKGROUND OF THE INVENTION

Inorganic peroxide is usually defined as hydrogen peroxide and adducts thereof. Some examples are: hydrogen peroxide, carbamide peroxide, sodium percarbonate, sodium perborate. Peroxide is used in many different applications from an antiseptic for minor wounds to bleach for teeth, hair and laundry. Solutions of varying strengths of hydrogen peroxide are readily on the market, usually in a liquid form.

For targeted bleaching applications, such as tooth whitening, it can be desirable to blend the peroxide into a gel by blending the peroxide with a thickener. Blending is accomplished by mixing the thickener with the peroxide, usually also with water or an appropriate organic solvent. However, due to the volatile oxidizing nature of peroxide (which imparts the substance's bleaching ability); there are very few thickeners that can withstand a peroxide environment. Most polymers will degrade quickly in a peroxide environment and will lose their thickening properties entirely due to the powerful oxidizing effects of peroxide. These gels will degrade into thin, water-type consistencies. It is rare to find a polymer that can withstand, for prolonged periods of time, the powerful effects of peroxide.

Chemists have diluted hydrogen peroxide in order to tame its instability and raw oxidizing power. Liquid hydrogen peroxide is common and is by far the most aggressive oxidizer and the most unstable. Chemists have also produced adducts of hydrogen peroxide to stabilize hydrogen peroxide in the resultant compounds. The main adducts of hydrogen peroxide that are used for bleaching are: urea hydrogen peroxide (carbamide peroxide), sodium perborate, and sodium percarbonate. However, dilution of hydrogen peroxide by any means, while increasing stability, also reduces the bleaching efficacy of resultant gels. Carbamide peroxide contains about 36% hydrogen peroxide by weight. Therefore, a bleaching gel made with about 10% carbamide peroxide (which is an industry standard), yields only about 3% hydrogen peroxide. Sodium percarbonate has an even lower concentration of hydrogen peroxide. The use of these adducts then, generates an instant upper limit to the final concentration of hydrogen peroxide in a product.

Dental whitening manufacturers have predominately been using carbamide peroxide. Carbamide peroxide is docile enough to be used with many polymers that would not work with hydrogen peroxide. The most used commercial thickener, CARBOPOL, is a good example of this. CARBOPOL is a good thickener for carbamide peroxide. However, CARBOPOL does not hold up to pure hydrogen peroxide for even short amounts of time. When CARBOPOL is used in a composition containing 30% hydrogen peroxide, the composition will begin to break down and form peroxide decomposition bubbles in about two weeks. Therefore what is needed is a polymer that is capable of withstanding hydrogen peroxide compositions for moderate amounts of time.

The direct application of these manufactured gels and liquids to the teeth for the purpose of bleaching does have drawbacks. Direct delivery of these gels and liquids onto the teeth can be unsuccessful as they tend to run-off the teeth by the force of gravity. They also are subject to being wiped off quickly by the cheeks and gums. To make matters worse, the saliva is also there to quickly wash and dilute any treatment fluids off of the teeth. While gels may be more resistant to these drawbacks as compared to other liquids, they still have these inherent difficulties.

In order to overcome the difficulties inherent in the direct application of fluidic treatment materials various inventions have been developed. One of the early inventions involved an insoluble barrier that would hold the treatment gels and liquids against the teeth and at the same time protect it against the tongue, cheek and saliva. This resulted in the invention of the plastic dental tray. The major drawback in the concept of a tray is that the variations in teeth anatomy make it very difficult to make and design a generic one-size-fits-all tray. Therefore some of the early trays were designed to fit onto the gums and mechanically pinch the gums in order to hold the tray onto the teeth. These mechanical trays were cumbersome and painful for patient use and became obsolete in favor of the custom tray. The custom tray involves creating an impression of the teeth, followed by casting a mold of said impression. Said mold is then covered with a pre-heated semi-molten plastic sheet with a vacuum in place in order to force the plastic to adapt to the casting's surface. Finally, the post-solidified tray is usually trimmed with scissors into a custom tray for a specific individual. The drawback to the custom tray is the amount of time and resource and effort needed to create one. The biggest drawback inherent in all trays of the prior art is their accompanying use of fluidic treatment gels and liquids. Once a tray is created it must be filled with a fluidic treatment gel or liquid and, most of the time, the patient must do this.

Early dental treatment products were liquids. Liquids were most especially difficult to handle, as they tend to run out of the trays and were easily spilled while filling the trays. Liquids were abandoned as the product of choice in favor of higher viscosity fluidic gels. Gels provide more control over flow characteristics than liquids. A gel can obtain higher viscosities that limit the flow of treatment products thereby allowing the treatment product to remain in the tray better. A gel also adds the benefit of some adhesion between the tray and teeth aiding in holding the tray in place once fitted. The drawback inherent to these fluidic gels and liquids is that they are messy for both patient and practitioner. When these fluidic gels and liquids spill while filling the tray or express out of the tray while fitting and wearing the tray; they are a nuisance and a complaint of patients. These are the drawbacks of fluidic treatment products and trays:

a. While filling trays, any spill is messy and a nuisance to clean up.
b. When fitting the filled tray onto the teeth, the teeth must displace the treatment fluids and any excess gel or liquid will be forced out of the tray and into the mouth. In the case of gels this becomes especially messy, since it cannot be easily spit or rinsed out. The current procedure calls for a toothbrush to agitate the gel and with copious amounts of dilution water, the patient will eventually work away the excess gel.

c. While wearing the trays, the upper teeth constantly come in contact with the lower teeth in a natural repetitive soft biting action. This natural biting action acts as a pump that when compressed will force more messy gel or liquid material out of the tray where it must be cleaned off or drowned in saliva. When the compression ends and the trays relax back into equilibrium it will either begin to empty out the tray and fill it with saliva (so the upper portion of the teeth are not treated) or they begin mixing and dilute the active ingredients.

Another invention of the prior art that is used to deliver treatment gels and liquids is the dental strip. The dental strip is an insoluble flexible plastic strip onto which the treatment fluidic gels have been applied. Liquid treatment products obviously would not work well with strips, since they would just run-off the strip. The dental strip is then applied to the teeth. Current dental strips even incorporate in their design shallow pockets into the plastic strip in order to hold fluidic treatment gels. The lack of these shallow pockets would limit the amount of treatment gel available for actual treatment after fitting the strip in place, as most of the gel would be displaced from a smooth surface during fitting. The drawbacks of these prior art dental strips are again their reliance on gels for functionality. Gels suffer from many of the same problems as trays, in that while fitting and wearing the strip any excess gel that is displaced or pumped out ends up in the mouth as a constant mess. In some respects the strips are worse than the trays, since they are not tray shaped they must hold their shape against the teeth by either the adhesiveness of the gel or the rigidity of the backing material or they tend to unfold off the teeth during use. Strips that use gels also suffer from movement on the teeth during use. The gels act as a slimy lubricant between the teeth and strip, which allows the strip to annoyingly move around while it is being worn. Patients complain when they have to constantly adjust the strip back into place. One of the biggest complaints with strips that use gels is with patients with uneven teeth, the strip tends to favor the tooth that sticks out and fails to contact adjacent teeth creating a gap between the strip and teeth that allows saliva to enter, which dilutes and washes away the gel.

Other disclosed inventions include more rigid or solidified treatment compositions that are set into a tray or onto a backing material. These solidified compositions can be sufficiently rigid as to maintain itself in a tray-like configuration absent their external supports. Others disclose a strip or a tray with a two-part treatment composition that is mixed and applied to the backing material just prior to use. These 2-part prior art compositions are incapable of being combined in a pre-mixed shelf stable treatment device. When combined, the resultant compound eventually sets to a rubber-like consistency and is placed against teeth; however, this is an unstable state. Over time, the compound decomposes into a dry powder and degraded peroxide. This is why this type of prior art system must be separated into 2 parts and mixed only upon patient use. These systems require the patient or clinician to make/mix the rubber-like substance first and then somehow load this same rubber-type consistency compound onto a whitening device prior to application to the patients teeth—this is too cumbersome.

These more rigid treatment compositions are an improvement over gel or liquid compositions, since they resist flow they tend to stay on the backing strip or tray when fitting and wearing the implements. So they do not pump out of the tray or displace out of the dental strip when fitting. However, they do crack and break if flexed. The odd product is the dry or wet type patches that do not have a backing strip or tray. The drawback to patches is that they do not have a barrier between the back of the patch and the mouth; therefore they are again subject to the wiping effect of adjacent oral tissues and the washing and dilution effects of saliva. Another drawback is the lack of barrier means not only the active ingredient is treating the teeth but also treating all the oral tissues on the other side. Many of these active ingredients are irritating or harmful to soft tissue; the patch is not much of an improvement over gels and liquids that are placed in strips or trays.

The drawback to more rigid treatment compositions placed in trays or dental strips is that they are limited to non-toxic, active ingredient stable, water-soluble thickeners of the prior art. Many of these thickeners have physical characteristics so that when they are dried from an aqueous state, they are not ideal for a tray or a dental strip. The ideal thickener would have these characteristics:

a. Adhesion in aqueous environment: that when the surface of the more rigid composition becomes wetted it becomes sticky. Many thickeners do not have sufficient stickiness to overcome the forces exhibited while fitting and wearing a tray or strip to uneven teeth. The adhesion should be great enough to hold the backing strip or tray to all varieties of teeth whether straight or crooked.

b. Hygroscopic: The water-soluble thickener should be able to resist drying to a powder over long periods of storage before use. Many thickeners tend to dry out even when sealed in their packages over time leaving condensation inside the package or may even just escape the packaging altogether. A hygroscopic thickener allows you to use and keep water in the formulation during storage because hygroscopic gels will retain an aqueous equilibrium of internal water and resist drying to a powder. This amount of internal water can be adjusted as it is directly proportional to the drying temperature; therefore, drying times and temperatures can be adjusted to adjust the visco-elasticity of the final product. Thickeners that dry out are limited to formulations that contain non-volatile solvents to keep them intact. The problem with these formulations is they tend to wet more slowly reducing short-term adhesion. Many thickeners will not even create a gel without water as one of the solvents.

c. Compatible with organic solvents: The ideal thickener should be able to incorporate organic solvents to manipulate and adjust various properties. These water-soluble thickeners that can also incorporate organic solvents are adjustable in their elasticity, plasticity, solubility, tackiness and viscosity by the appropriate use of various organic solvents. A water-soluble thickener that does not incorporate organic solvents is left with only water as the modifier of choice.

d. Elasticity: The ideal thickener would have sufficient elasticity, without splitting or cracking during storage or while fitting the implement. Some devices of the prior art are of a composition that has a rigidity so as to maintain itself in the shape of its container even when the external support is removed. These compositions have essentially dried out and are solid and brittle. Many rigid compositions of the prior art are dried solids adjacent a strip or tray. The backing strip and tray are usually flexible yet the dried composition is brittle and tends to crack when manipulating the implement. There is a drawback to dry and brittle compositions in that they need lots of water to become hydrated to a point where the active ingredients become "active". These dry compositions will tend to draw the water out of the initial wetted layer, thus drying out the surface into a less mobile layer. Also many active ingredients are volatile and would simply evaporate when dried; others are only stable in the presence of water and would inactivate the product if it were dried out. Finally a dried composition tends to lose its adhesiveness and become loose from the backing strip or tray and falls out.

What is needed is a thickener that demonstrates all of the above characteristics that can be conjoined to a film, backing strip, backing sheet or tray in order to more efficiently deliver the active ingredients to the teeth and gums. Poly(2-ethyl-2-oxazoline) is a water soluble thickener with ideal properties attuned to the creation of pre-mixed, shelf stable compositions that may take the form of gels, visco-elastic and gelatinous compositions, that are intended to release an active ingredient. These compositions can be matched to a backing material in various designs and shapes such as a tray or dental strip.

The present invention represents a departure from the prior art in that the application of the present invention in peroxide gels allows for higher peroxide concentrations by providing a gel base that is surprisingly stable in a peroxide environment. The resultant gels may use pure hydrogen peroxide at concentrations where only adducts have been used in the prior art, thereby doubling or tripling the resultant concentration of hydrogen peroxide in the finished product while simultaneously providing comparable or superior gel stability. The present invention also presents the gels in a stable, gelatinous, visco-elastic form that is easily packaged and stored, and provides a delivery system for the same. When placed on a flexible backing, the gelatinous active component acts as a flexible adhesive that will adhere to a user's dental arch and have the thickness and elasticity to remain in place. The final product, then, is a conformable dental treatment tray that will shape itself to any particular irregularities of a user's dental arch. Therefore, it is truly customizable for the user, unlike prior art constructs.

For purposes of this Application, the term "gelatinous" shall have the definition given first in the American Heritage Dictionary of the English Language, Fourth Edition, © 2006 by Houghton Mifflin Co.: "resembling gelatin, viscous." A gelatinous compound shall be a visco-elastic compound having physical deformation properties between a solid and a fluid. A solid shall be defined as a substance that is sufficiently rigid so that it maintains its form indefinitely, independent of any structure or support. A fluid shall be defined as a substance that will conform and coalesce to the shape of a beaker into which multiple samples of the same substance are placed, within 10 minutes, with hand agitation of the container and/or hand mixing with an implement at 25° C. with an atmospheric pressure of 1 ATM. Therefore, a gelatinous compound, as the term is used in this Application, will have some degree of flex and deformation as required to fit inside a container, but will not coalesce so that a specific sample or portions thereof are still determinable. This is particularly evident if a number of discrete units of gelatinous material are placed in a container—they will bend as they contact the container but will not merge into one body.

SUMMARY OF THE INVENTION

In view of the foregoing disadvantages inherent in the known types of thickeners for peroxide gels, this invention provides an improved thickener. As such, the present invention's general purpose is to provide a new and improved thickener that is capable of maintaining a gel consistency for a peroxide gel while allowing for higher peroxide concentrations to increase efficacy.

Chemical solutions and gels containing hydrogen peroxide are well known in the art. In principle, the solutions and gels are made by combining a peroxide, solvents and a thickening agent. Varying degrees of viscosity and strength are easily generated by altering the base components' proportions and identities. For the purpose of this application, the preferred embodiment will be described as a dental whitening gel, though many other applications may be easily conceived and should be deemed to be included in this Application and its claims. Such additional applications include bleaching products for hair or laundry, where viscosity may not be as important as with a dental gel, but the principles and invention described herein, namely higher viscosity and bleaching strength, are equally applicable.

The novel thickening agent is Poly(2-ethyl-2-oxazoline). It is a polymer that swells upon absorption of liquids. Poly(2-ethyl-2-oxazoline) creates very viscous gels. There are many different molecular weights of Poly(2-ethyl-2-oxazoline) available commercially. These can be chosen to impart different physical properties to the gel for bleaching and other applications.

Poly(2-ethyl-2-oxazoline) is surprisingly a polymer that is capable of excellent compatibility with peroxide and imparts excellent thick viscous properties to the gel. Experience has shown that a 30% hydrogen peroxide gel made with Poly(2-ethyl-2-oxazoline) stays a gel during six month's storage at room temperature. Poly(2-ethyl-2-oxazoline) is a superior polymer in an oxidizing peroxide environment to current thickening polymers like CARBOPOL, silica, PVP, and polyethylene glycols.

One particular use of the combination of Poly(2-ethyl-2-oxazoline) and peroxide, and the focus of this application, is the creation of a formable dental treatment tray for the purpose of treating teeth. When peroxide is mixed with Poly(2-ethyl-2-oxazoline), with a solvent in the case of powdered peroxides, and the resulting combination is appropriately dried, the resultant product is a hygroscopic, gelatinous, visco-elastic substance that is less adhesive than a gel, is well packaged, relatively inert and behaves well in product production. When water is added to the surface of the substance, the substance regains the adhesiveness lost in the drying process and may be applied directly to a user's teeth in a manner that conforms to that individual user's dental arch. The gels may be applied to a tape-like backing, such as PARAFILM, dried, cut into appropriate shapes, like a strip, and packaged for a particularly effective bleaching tray to be used in clinical or home applications.

Packaging of the product must resist moisture as the hygroscopic nature of the product will tend to absorb atmospheric moisture and alter its visco-elastic qualities.

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims. Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

The preferred embodiments of the peroxide gels used to create the deformable trays according to the precepts of this invention are herein described. It should be noted that the articles "a", "an" and "the", as used in this specification, include plural referents unless the content clearly dictates otherwise.

Poly(2-ethyl-2-oxazoline) is commercially available in 50,000, 200,000 and 500,000 M.W. Varying viscosities and longevity of gels may be created based on the amount and weight of Poly(2-ethyl-2-oxazoline) used and the desired strength of peroxide. As a guide, dental gels are preferred to be a viscosity between 1000 and 200,000 centipoise. In such ranges, peroxide concentrations may reach up to 50% hydrogen peroxide using Poly(2-ethyl-2-oxazoline) as a thickener. In its preferred form, a 30% concentration may be obtained with a shelf life of six months at room temperature. The simplest preferred gel is obtained by mixing 50% strength hydrogen peroxide with 200,000 M.W. Poly(2-ethyl-2-oxazoline) in a ratio of 6:4. Additional strengths of peroxide gels may be obtained by utilizing additional solvents and different molecular weights of Poly(2-ethyl-2-oxazoline). Some common solvents include: water, ethanol, polyethylene glycols, polypropylene glycols, glycerin, and propylene glycol. Any of these may be added for varying the consistency and properties of the gels created. However, each gel must be developed with the basic limitation that the strength of the peroxide in the gel makes the gel inherently more unstable.

Figure 1:
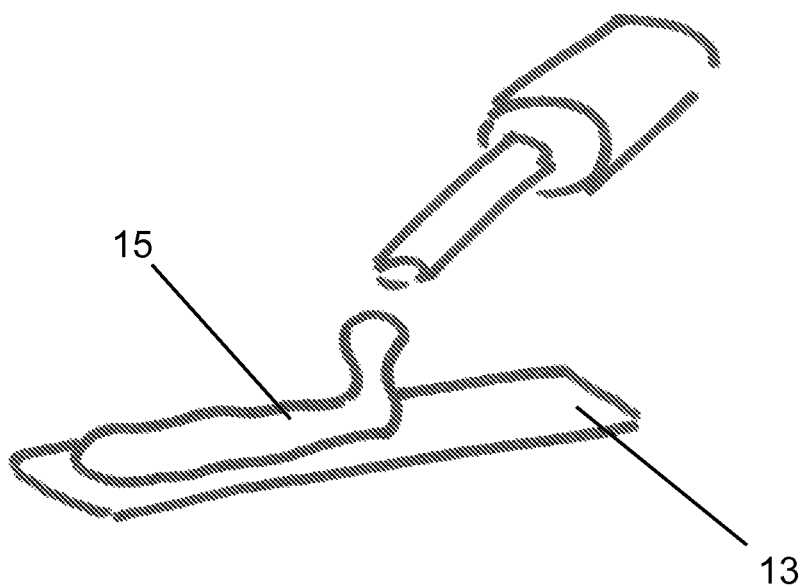
FIG. 1 is a perspective view of gel being placed on a backing to create a tray according to the present invention.
Figure 2:
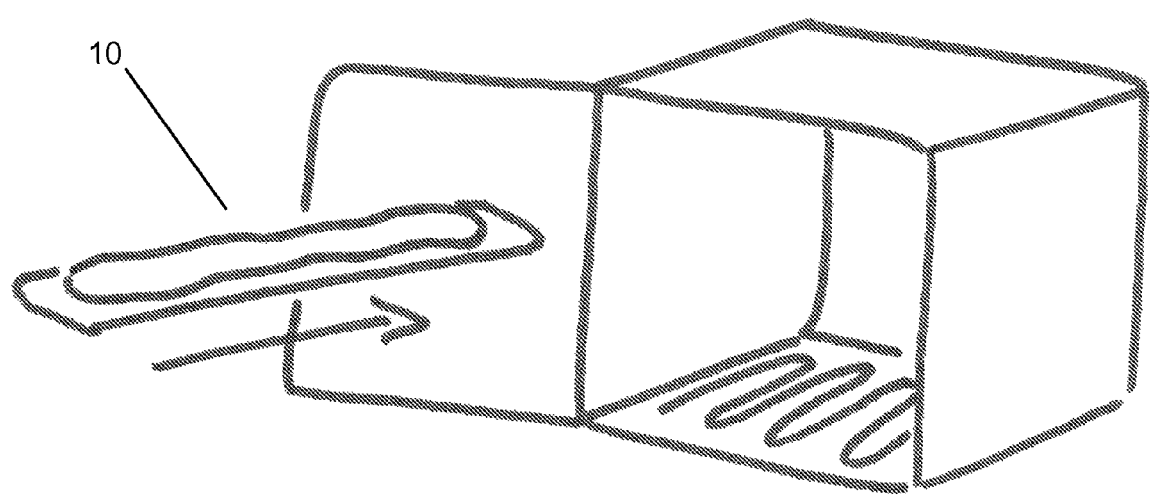
FIG. 2 is a perspective view of the tray of FIG. 1 being dried.
Figure 3:
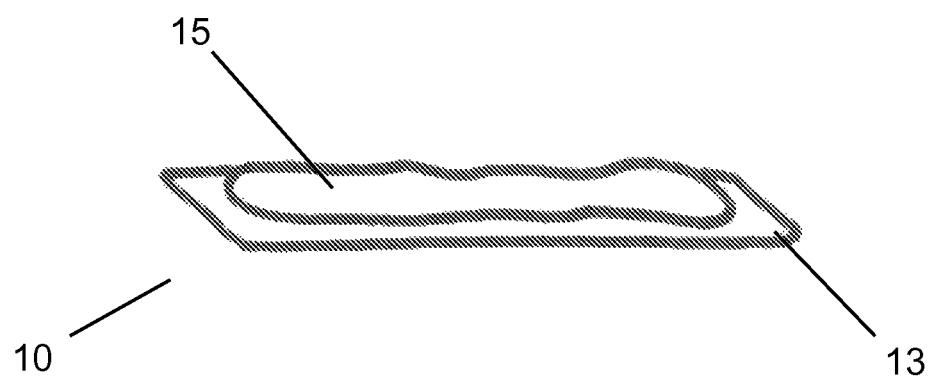
FIG. 3 is a perspective view of a finished tray.

In the present invention, the resultant gels 15 are placed on preformed pieces of a backing 13, such as PARAFILM (a polymeric wax mixture), as shown in FIG. 1. The backing provides stability for the resultant substance and a surface with which the tray may be touched for manipulation. The gels 15 are then dried through conventional processes. Typical drying may be performed at temperatures of approximately 37° C. for 12 to 24 hours (FIG. 2). Drying may also take place in any other suitable environment, including those of ambient air, room temperature, lower than room temperature, higher than room temperature, or vacuums. Times and temperatures may vary for individual gel composition. When dried, the gels form a bleaching compound that will conform to a user's dental arches and form a bleaching tray 10 without cracking or breaking (FIG. 3). The resultant compound is visco-elastic, and gelatinous, having a flexibility and consistency similar to the popular confection known as gummi worms, and will deform when removed from the backing material. The resultant tray is initially planar; with a significant body of gelatinous whitening composition adhered to the backing.

Figure 4:
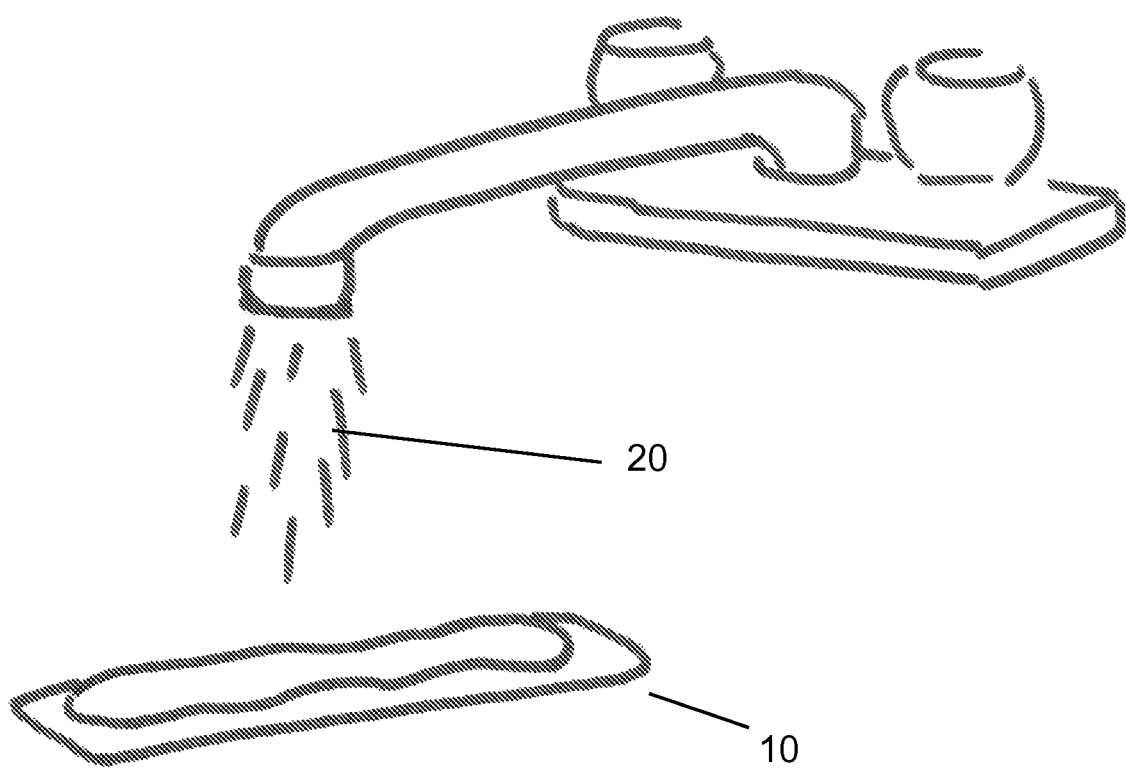
FIG. 4 is a perspective view of the tray of FIG. 3, being hydrated.
Figure 5:
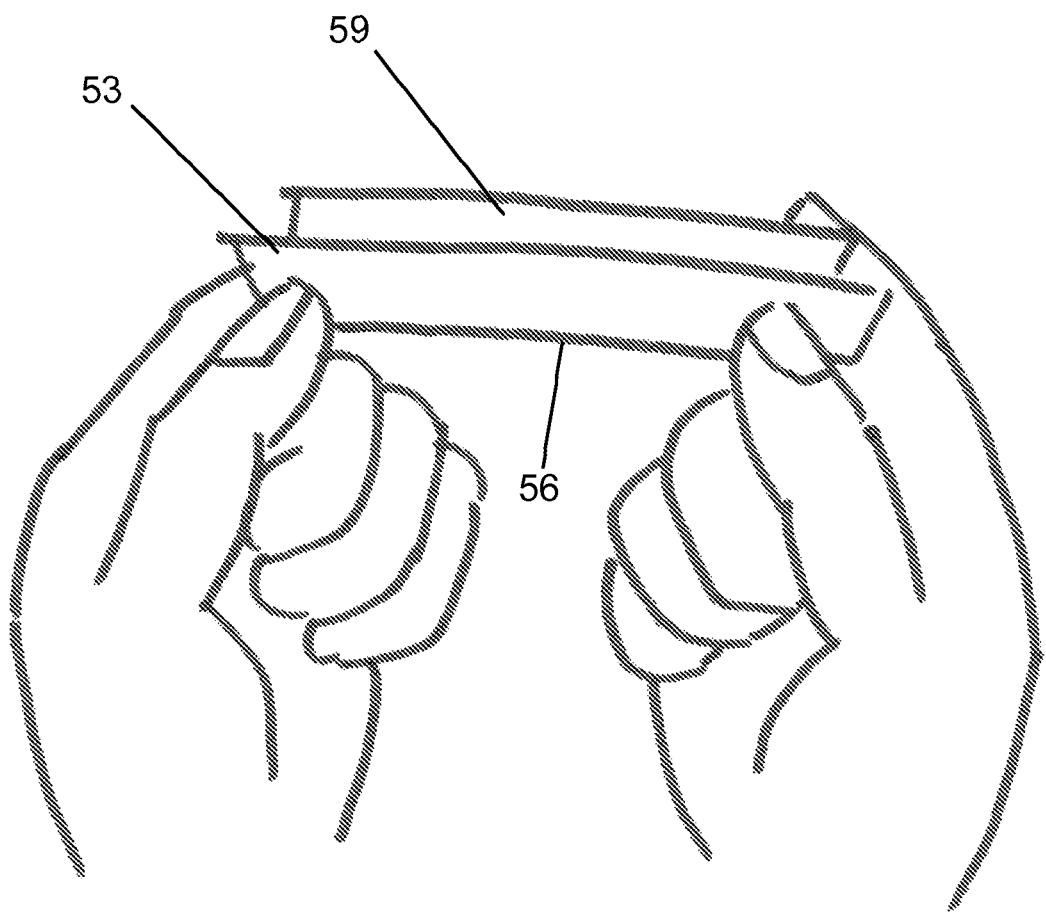
FIG. 5 is a perspective view of the tray of FIG. 4, being folded prior to positioning.
Figure 6:
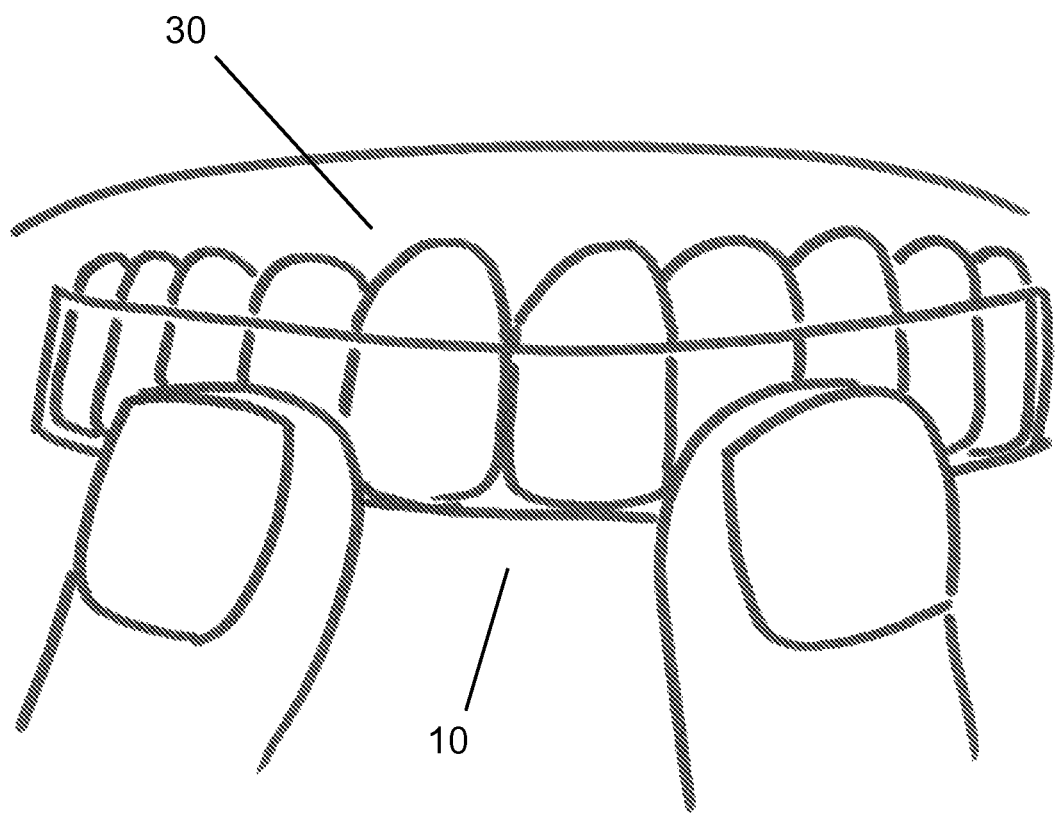
FIG. 6 is a perspective view of the tray of FIG. 2 being formed to a user's upper dental arch.

In use, FIGS. 4-6, a user will take a tray 10 and wet it with water 20. The gel will rehydrate and become more adhesive so that the tray will then be applied to the user's teeth (dental arch 30). The user will press and form the tray 10 around the dental arch 30 (FIG. 6), conforming it to the individual shape of the arch 30 and, ideally covering at least one, if not both, sides of the arch 30. The user may, if desired, pre-fold the tray (FIG. 5) before applying it to the teeth. The tray 10 according to the present invention is therefore totally customizable and formable, creating a buccal wall 53, a crease/bottom 56 and a lingual wall 59. These walls and floor conform exactly to the user's dental arch 30 (FIG. 6), mimicking the variations and individualities of a particular user's arch. Once treatment is completed, the user simply removes the tray. Additional water may be needed to complete removal due to the adhesiveness of the tray 10.

Due to the increased peroxide content in the whitening compound, time of treatment will be less than conventional prior art whitening methods. Treatment may be accomplished in three days, rather than over the course of a week. As always, a second round of treatment may be initiated, but it is recommended that a user wait at least one day between courses of treatment due to the increased potency of the product. Longer treatment times and courses may be utilized with lower concentration peroxide gels and may extend as long as a week of consecutive treatments.

By way of example, the following formulations are supplied as examples of compositions for the gel according to the present invention. A true best mode will be dependent upon the desired attributes of the gels, and eventual trays, created. However these examples of possible gels all have the required consistency and bleaching power required by the present invention. It is, of course, to be understood that the following list is only for illustration and that any variation of these and other gels will fall within the purview of this invention. Accordingly, it is to be understood that those skilled in the art will be capable of formulating an infinite number of possible gels and, as such, this list should not in any way be deemed limiting of the invention.

(Composition in % by weight)

Formula #1
1. 11%—Carbamide Peroxide
2. 43%—Poly(2-ethyl-2-Oxazoline) M.W. 500,000
3. 27.5%—Purified or distilled water
4. 16.7%—Ethanol
5. 1.0%—Poly acrylic acid 35% M.W. 100,000
6. 0.3%—Sucralose
7. 0.4%—Peppermint Oil USP
8. 0.1%—Potassium Hydroxide USP Formula #2
1. 17%—Carbamide Peroxide
2. 40%—Poly(2-ethyl-2-Oxazoline) M.W. 500,000
3. 25.5%—Purified or distilled water
4. 15.7%—Ethanol
5. 1.0%—Poly acrylic acid 35% M.W. 100,000
6. 0.3%—Sucralose
7. 0.4%—Peppermint Oil USP
8. 0.1%—Potassium Hydroxide USP Formula #3
1. 23%—Carbamide Peroxide
2. 37%—Poly(2-ethyl-2-Oxazoline) M.W. 500,000
3. 23.25%—Purified or distilled water
4. 14.7%—Ethanol
5. 1.0%—Poly acrylic acid 35% M.W. 100,000
6. 0.3%—Sucralose
7. 0.4%—Peppermint Oil USP
8. 0.1%—Potassium Hydroxide USP
9. 0.25%—Sodium Fluoride USP Formula #4
1. 27%—Carbamide Peroxide
2. 33%—Poly(2-ethyl-2-Oxazoline) M.W. 500,000
3. 25%—Purified or distilled water
4. 13.2%—Ethanol
5. 1.0%—Poly acrylic acid 35% M.W. 100,000
6. 0.3%—Sucralose
7. 0.4%—Peppermint Oil USP
8. 0.1%—Potassium Hydroxide USP Formula #5
1. 17%—Carbamide Peroxide
2. 50%—Poly(2-ethyl-2-Oxazoline) M.W. 200,000
3. 20.5%—Purified or distilled water
4. 10.7%—Ethanol
5. 1.0%—Citric acid 35% M.W. 100,000
6. 0.3%—Aspartame
7. 0.4%—Peppermint Oil USP
8. 0.1%—Potassium Hydroxide USP Formula #6
1. 27%—Carbamide Peroxide
2. 33%—Poly(2-ethyl-2-Oxazoline) M.W. 500,000
3. 25%—Purified or distilled water
4. 13.2%—Ethanol
5. 1.0%—Malic acid 35% M.W. 100,000
6. 0.3%—phenyl alanine
7. 0.4%—Banana Flavoring
8. 0.1%—Sodium Hydroxide USP Formula #7
1. 11%—Hydrogen Peroxide
2. 43%—Poly(2-ethyl-2-Oxazoline) M.W. 500,000
3. 27.5%—Purified or distilled water
4. 16.7%—Ethanol
5. 1.0%—Poly acrylic acid 35% M.W. 100,000
6. 0.3%—Sucralose
7. 0.4%—Peppermint Oil USP
8. 0.1%—Potassium Hydroxide USP As can be seen, other ingredients include flavorings and sweeteners, solvents, plasticizers, and other elements for desired effect. It is, of course, readily conceived that other active ingredients may be added to the composition for more desired effects, with or without peroxide. Such active ingredients may include and are not limited to fluoride, desensitizers, anti-microbials, anti-fungals, re-mineralizers, surfactants, nutraceuticals, pharmaceuticals and other medicaments. While it is not as preferred as Poly(2-ethyl-2-Oxazoline), polyvinylpyrrolidone ("PVP") may be used in this invention with good results. Again, proportions in formulas using PVP will vary according to desired characteristics and purposes.

A specific list of possible additives includes, but is not limited to:

Fluorides—sodium fluoride, potassium fluoride, Stannous fluoride, sodium monofluorophosphate and alkyl fluoroamines.

Desensitizers—potassium citrate, glutaraldehyde, sodium citrate, potassium nitrate, sodium nitrate and Sodium and potassium salts of EDTA, and EDTA.

Anti-microbials—chlorhexidine, chlorhexidine gluconate, benzalkonium chloride, thymol, sodium chlorite, potassium chlorite, triclosan, methyl paraben, propyl paraben, sodium benzoate, benzalkonium chloride, cetyl pyridinium chloride, zinc chloride.

Anti-fungals: Ketoconazole, potassium permangante, terninafine HCL, zinc chloride Re-mineralizers—potassium sucrose phosphate, sodium sucrose phosphate, sodium phosphate mono basic, sodium phosphate dibasic, sodium phosphate tri-basic, alone or in combination with one or more of the following: calcium fluoride, calcium hydroxide, calcium hydroxy apatite, sodium fluoride, potassium fluoride, sodium monofluorophosphate.

Surfactants—sodium lauryl sulfate, Polysorbates, Lauryl dimethyl amine oxide, Cetyltrimethylammonium bromide, Polyethoxylated alcohols, Polyoxyethylene sorbitan Octoxynol, N,N-dimethyldodecylamine-N-oxide, Hexadecyltrimethylammonium bromide, Polyoxyl 10 lauryl ether, Polyoxyl castor oil, Nonylphenol ethoxylate, Cyclodextrins, Lecithin, Methylbenzethonium chloride.

Pharmaceuticals—Amoxicillin, amoxil, biaxin, cefzil, cipro, levaquin, minocycline, penicillin, tetracycline, trimox, zithromax, astringent alums.

Nutraceuticals—ascorbic acid, B-glucan, lutein, gallic acid, aloe Vera, lactobacillus acidophilus, zinc, tocopherol, choline, Q-10, B-carotene, lycopene, sodium carbonate, glutathione.

Sweeteners: sucrose, glucose, fructose, phenyl alanine, sucralose, sodium saccharin, xylitol.

Flavors—peppermint oil, methyl salicylate, spearmint oil, cinnamon oil, artificial and natural fruit flavorings like banana flavoring, peach flavoring, and apple flavoring.

Although the present invention has been described with reference to preferred embodiments, numerous modifications and variations can be made and still the result will come within the scope of the invention. Such modifications include increasing or decreasing viscosity and peroxide concentration for various purposes. No limitation with respect to the specific embodiments disclosed herein is intended or should be inferred.

What is claimed is:

1. A dental fluoride delivery device, comprising:
   a backing material; and
   a dental composition in contact with the backing material, wherein:
   the dental composition comprises Poly(2-ethyl-2-oxazoline) and fluoride; and
   the dental composition is a gelatinous compound having physical deformation properties that allow the dental composition to bend and conform to a shape of a container into which the dental composition is placed, but the dental composition will not merge into a second piece of the dental composition when placed in contact with the second piece.

2. The dental fluoride device in claim 1, wherein the backing material is made from a polymeric wax mixture.

3. The dental fluoride device in claim 1, wherein the fluoride is in the form of a fluoride source being selected from the list of fluoride sources consisting of: sodium fluoride, potassium fluoride, stannous fluoride, sodium monofluorophosphate and alkyl fluoroamines.

4. A dental fluoride delivery device, comprising:
   a backing material made from a polymeric wax;
   a dental composition located on the backing material, comprising:
   Poly(2-ethyl-2-oxazoline);

fluoride; and
a solvent;
wherein, the dental composition is a gelatinous compound.

5. The dental fluoride delivery device in claim 4, wherein the dental composition becomes more adhesive upon wetting the dental composition with water.

6. The dental fluoride delivery device in claim 5, wherein the dental fluoride delivery device is sized to conform to an individual's dental arch.

* * * * *